United States Patent [19]
Rader et al.

[11] Patent Number: 5,563,584
[45] Date of Patent: Oct. 8, 1996

[54] LIQUID LEVEL SENSING AND MONITORING SYSTEM FOR MEDICAL FLUID INFUSION SYSTEMS

[75] Inventors: R. Scott Rader, Baltimore, Md.; Eric H. Schallen, Ann Arbor, Mich.; Alexander C. Walsh, Hunt Valley, Md.; Carl C. Awh, Lutherville, Md.; Eugene de Juan, Phoenix, Md.

[73] Assignee: The Johns Hopkins University, Baltimore, Md.

[21] Appl. No.: 152,012

[22] Filed: Nov. 15, 1993

[51] Int. Cl.$^6$ ............................................. G08B 21/00
[52] U.S. Cl. .................... 340/618; 340/611; 340/614; 340/626; 128/DIG. 13; 604/31; 604/67; 137/403; 73/299
[58] Field of Search ........................ 340/618, 611, 340/626, 614, 620; 128/DIG. 13; 604/65, 67, 31; 137/386, 403, 406; 73/299

[56] References Cited

U.S. PATENT DOCUMENTS

| | | | |
|---|---|---|---|
| 3,631,437 | 12/1971 | Campbell | 340/620 |
| 3,641,543 | 12/1972 | Rigby | 340/620 |
| 4,598,733 | 7/1986 | Kanno et al. | 340/626 |
| 5,060,512 | 10/1991 | Kanashige et al. | 340/614 |

*Primary Examiner*—Jeffery Hofsass
*Assistant Examiner*—Daniel J. Wu
*Attorney, Agent, or Firm*—Cushman Darby & Cushman, LLP

[57] ABSTRACT

A liquid level sensing and monitoring system for a medical fluid infusion system has an IV spike with a pressure sensor which contacts fluid in an infusion container such as an IV bag or bottle. When an adequate amount of fluid is in the container, the resulting pressure on the sensor is at a relatively high level; however, when the fluid reservoir is nearly depleted, the pressure on the sensor falls to a low level, thereby activating the sensor and associated control circuitry which operates an alarm or warning indicator. In lieu of the pressure sensor, the device may use a resistive or capacitive sensor. When the liquid level falls below the electrical sensor, its state changes, and the alarm circuitry is activated.

18 Claims, 5 Drawing Sheets

LIQUID LEVEL SENSING AND MONITORING SYSTEM FOR MEDICAL FLUID INFUSION SYSTEMS

BACKGROUND OF THE INVENTION

1. Field of the Invention

The present invention relates to intravenous infusion systems for introducing fluids into the human body, and more specifically, to level sensing and monitoring systems for detecting low levels of such fluids in containers supplying the fluids.

2. Description of the Related Art

The use of intravenous (IV) supply bags and bottles to introduce nutrient, therapeutic and medicinal fluids into the human body is well-known in the art. Typically, such systems have a container suspended above a patient by means of an IV bag stand or the like. The container is hung from the stand, and fluid flows from an IV spike inserted in the lower portion of the container through a delivery tube to an IV needle inserted into the patient, where it is infused into the patient's body.

To ensure a regular and uninterrupted flow of fluid to the patient, it is necessary to monitor the fluid level in the container so that it can be replaced when the fluid is low. Alternatively, the fluid in the container may be replenished. In either case, it is necessary to have an attendant continuously or periodically monitor the fluid level or provide an automated monitoring system. Common automated monitoring systems in use today are optoelectronic devices which monitor a clear portion of the delivery tube. When the fluid level falls below the IV spike fluid inlet port, air from the upper evacuated portion of the container enters the delivery tube. Upon detecting the bubbles in the delivery tube, the system activates an audible or visual alarm. It also may optionally terminate the fluid flow to avoid introducing the bubbles into the patient.

In an alternative system, the capacity of the container and a desired flow rate are used to calculate the period of time during which the flow can be maintained. The flow is initiated and controlled by an undulating track arrangement holding the IV line, and when the calculated time period elapses, the system activates an alarm.

While such systems are effective, they are not without disadvantages. For example, the systems are relatively complicated and consequently failure-prone. Moreover, they are expensive—in late 1993, an optoelectronic-type unit cost approximately $2000.

SUMMARY OF THE INVENTION

It is an object of this invention to provide a liquid level sensing and monitoring system for fluid infusion systems that is inexpensive and easily replaceable.

It is a further object of this invention to provide a fluid infusion monitoring system that has a simple and straight-forward structure.

It is a still further object of the present invention to make a simple, low cost monitor for infusion fluids that can work with a disposable IV bottle or bag spike, directly or indirectly contact the fluid, is small enough to be supported by the spike, and can sense the presence of different liquid levels.

The above objects are achieved by providing a modified IV spike having a gauge or differential pressure sensor attached thereto which directly or indirectly contacts the fluid in the infusion container. When an adequate amount of fluid is in the container, the resulting pressure on the sensor is at a relatively high level; however, when the fluid reservoir is nearly depleted, the pressure on the sensor falls to a low level, thereby activating the sensor and associated control circuitry which operates an alarm or warning indicator.

In an alternative embodiment of the invention, the mechanical pressure sensor is replaced by an electrical sensor responsive to resistive or capacitive properties of the infusion liquid. When the liquid level falls below the electrical sensor, its state changes, and the alarm circuitry is activated.

BRIEF DESCRIPTION OF THE DRAWINGS

These and other objects and advantages of this invention will become apparent and more readily appreciated from the following description of the presently preferred exemplary embodiments, taken in conjunction with the accompanying drawings, of which.

DETAILED DESCRIPTION OF THE PRESENTLY PREFERRED EXEMPLARY EMBODIMENTS

Figure 1:
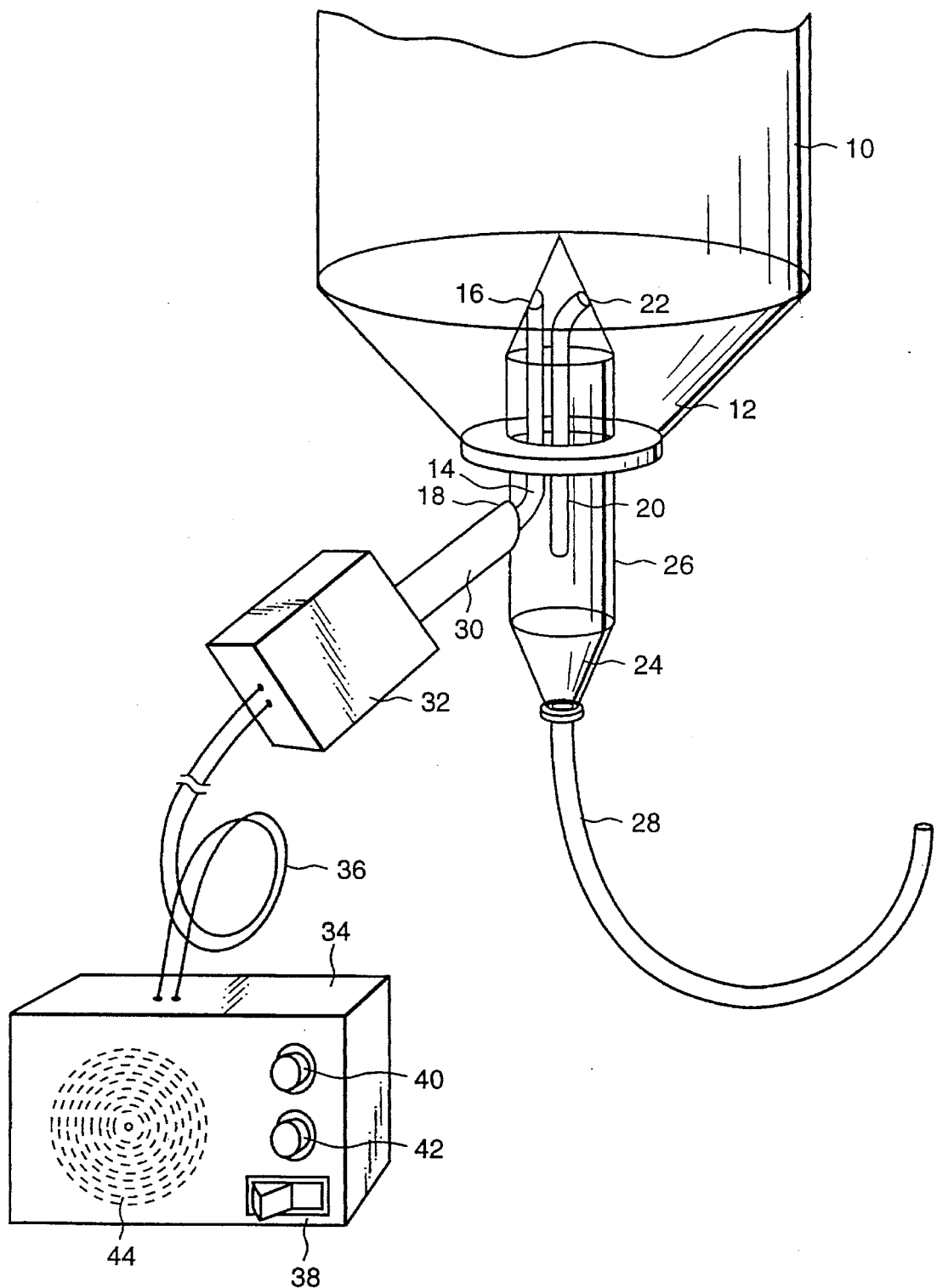
FIG. 1 is perspective view of a first embodiment of the present invention.

A first embodiment of the present invention is shown in FIG. 1, where a container 10 such as an IV bag has an IV spike 12 at its mouth. The spike 12 has a vent tube 14 connecting a vent inlet port 16 to a vent outlet port 18, a drip tube 20 having one end connected to a drip inlet port 22 and a second end proximate to a drip reservoir 24 at the lower end of a spike body 26. The drip reservoir 24 drains into a delivery tube 28 as described above. For clarity, the distal portion of the delivery tube 28 including the aforementioned IV needle is not shown in this Figure.

In a conventional IV spike, the inlet tube 14 has a ball-and-channel valve which permits air to be introduced through a microporous filter into the interior of the IV bag 10. This feature prevents the evacuation of fluid through the drip inlet port 22 from developing a vacuum in the upper portion of its associated container when used with a rigid container such as an IV bottle; however, the first embodiment of the present invention is preferably used with a container having collapsible sides such as the IV bag 10. Since the sides of the container collapse and reduce the volume of the evacuated space, no vacuum is created, and the vent port is not needed.

In this case, the valve can be replaced by a small piece of surgical tubing 30 connected to a pressure-sensitive sensor 32 such as a World Magnetics® PSF102-0.5-10" W. C. diaphragm switch. Although the valve should be removed, the vent ports usually include a hydrophobic filter such as an expanded PTFE microfiltration membrane made by W. L. Gore and Associates to permit air to enter the IV bag while preventing fluid from leaving it. The filter should be retained to avoid contamination of the fluid by the pressure switch.

The terminals of the switch 32 are electrically connected to an alarm unit 34 via cable 36. The alarm unit 34 has an ON/OFF switch 38 for activating the device, a POWER ON lamp or light emitting diode (LED) 40 which provides a visual indication when the device has operative power, and a LOW LEVEL lamp or LED 42 which provides a visual indication that the fluid level in IV bag 10 is low. The unit also includes a speaker 44 which provides an audible low level indicator. Preferably, the POWER ON and LOW LEVEL LEDs are distinguishable by color. Alternatively, the POWER ON LED may flash and the LOW LEVEL LED shine steadily.

Figure 2A:
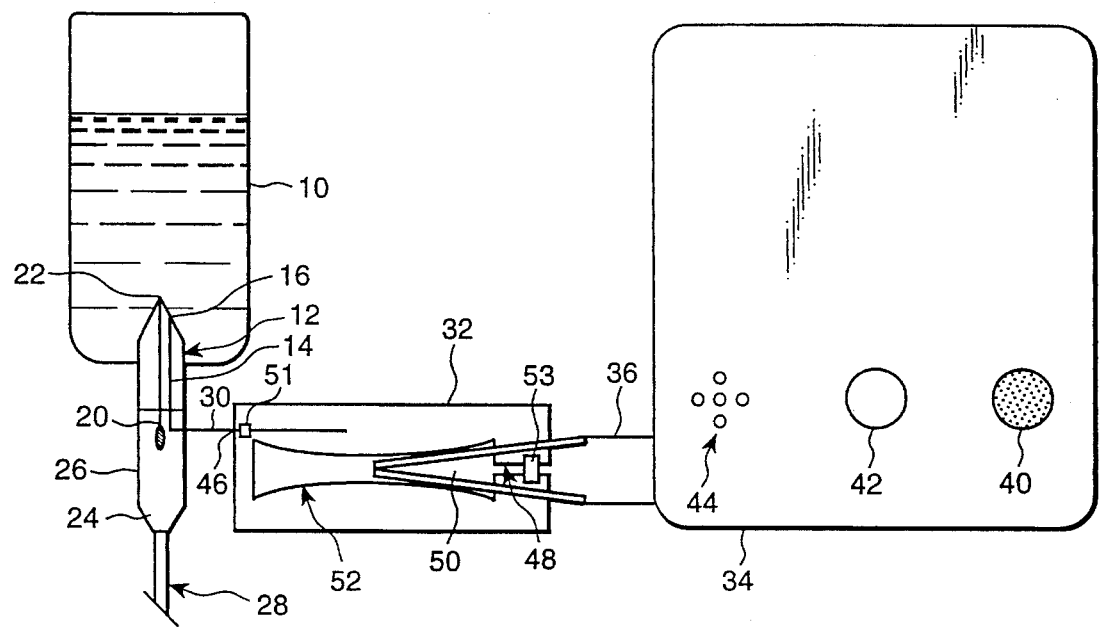
FIGS. 2A, 2B and 2C are schematic diagrams demonstrating the operation of a pressure-sensing system according to the present invention.
Figure 2B:
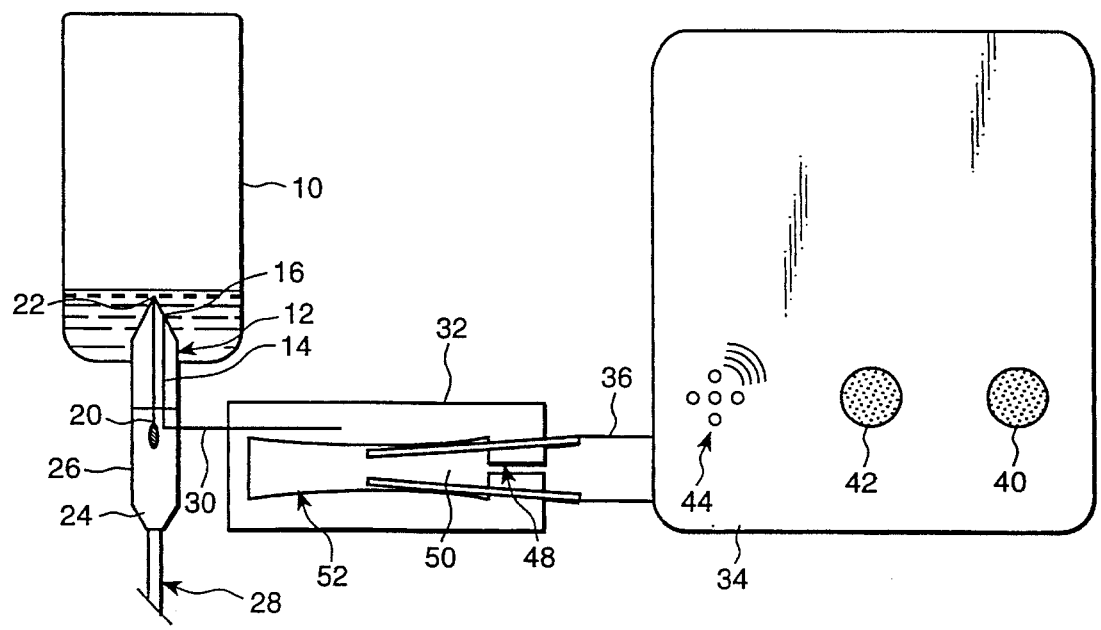

The construction and operation of the pressure sensor 34 can be seen more clearly in FIGS. 2A and 2B. These Figures show the surgical tubing 30 connecting the vent outlet port 18 to a high pressure port 46 of the pressure sensor 34, while a low pressure port 48 of the sensor 34 is left open to the atmosphere. In this manner, the sensor 34 acts as a gauge pressure sensor rather than as a differential pressure sensor.

Figure 2C:
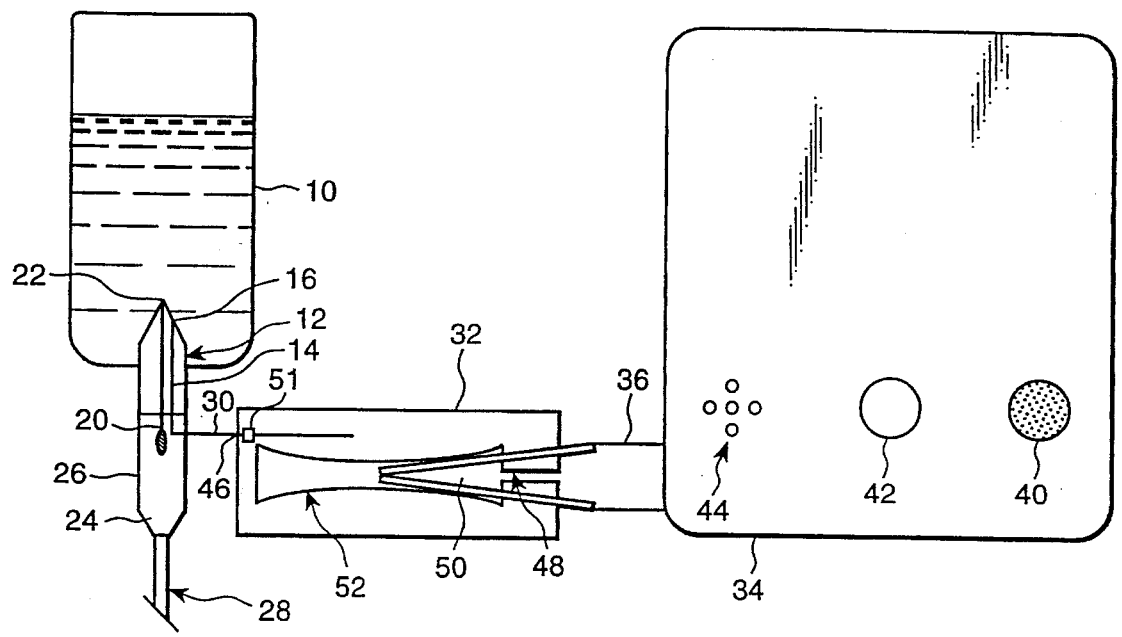

In an additional embodiment, a filter 51 is provided at the high pressure port 46 and a second filter 53 is provided at the low pressure port 48 to prevent contamination of the infusion liquid. Alternatively, only filter 51 is provided at high pressure port 46 as shown in FIG. 2C.

The cable 36 runs from two resilient conductive leaves 50, encased by a pressure diaphragm 52, to the alarm unit 34. The leaves 50 are resiliently biased to move away from one another; however, under normal IV supply conditions as shown in FIG. 2A (i.e., when the fluid supply is sufficient), the pressure exerted on the diaphragm 52 by the fluid forces the leaves 50 together to form a closed circuit. When the fluid in the IV bag 10 is low, however, the pressure it exerts against the leaves 50 is overcome by their resiliency, thereby opening the circuit as shown in FIG. 2B.

Figure 3:
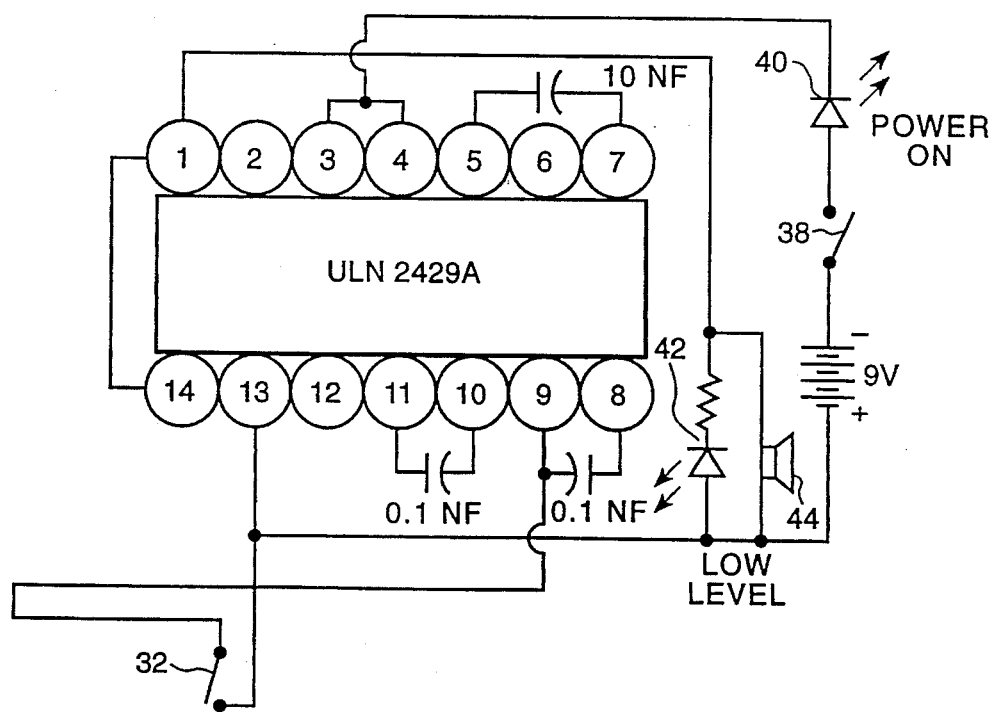
FIG. 3 is a schematic diagram showing alarm circuitry which may be used in the present invention.

FIG. 3 shows a circuit which may be used in the alarm unit 34. This Figure shows pressure switch 32, POWER ON LED 40, LOW LEVEL LED 42, speaker 44, and ON/OFF switch 38. This circuit preferably uses a ULN 2429A fluid detector integrated circuit. As the unit is preferably battery powered, it is advantageous to provide a low battery sensor and indicator in a manner that will be apparent to one of ordinary skill in the art.

While this embodiment of the present invention provides numerous advantages over the above-described prior art IV fluid monitors and it particularly well suited for some applications, its simplicity limits its flexibility for general use. For example, a version of this embodiment suitable for use in vitreoretinal surgery where the desired flow rate is relatively fast would require approximately a 1" fluid column in the IV bag 10 to give personnel adequate time to replace the bag. In contrast, a medication or nutrient application might require a low flow rate, and a warning is not needed until the fluid is further depleted. If a diaphragm switch is used as the pressure sensor 34, it generally is calibrated to respond to a predetermined pressure level above which it is in the open (or closed) state and below which it is in the closed (or open). Thus, a version of the device useful in vitreoretinal surgery might not be usable in other applications.

A variation on this embodiment overcomes this problem by providing a variable alarm range capability. By using a sensor 34 providing a continuously variable output signal over a range of pressures, the device can set a threshold pressure above which it is activated. Advantageously, the pressure sensor 34 is a differential pressure sensor using a piezoelectric or piezoresistive semiconductor device such as a Honeywell Micro Switch 24PC series unit. To use such a sensor, the alarm unit circuitry shown in FIG. 3 should be modified to provide a variable threshold level using, for example, a potentiometer and comparator arrangement in a manner that will be readily apparent to one of ordinary skill in the art.

Figure 4:
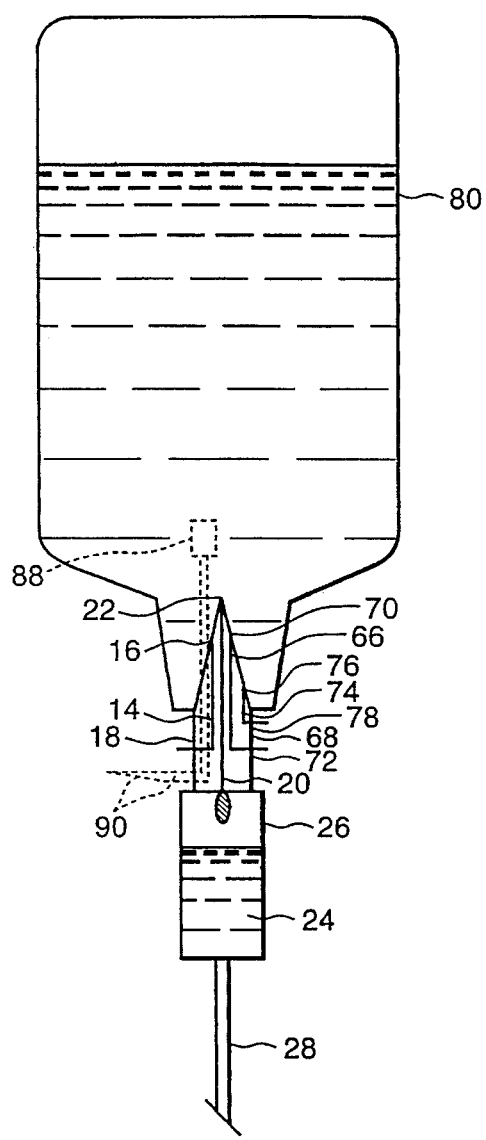
FIG. 4 is a schematic diagram demonstrating the operation of the second embodiment of the present invention.

The above designs are useful in monitoring IV bags and similar containers which have collapsible side walls, since the pressure of the evacuated upper portion of such bags is roughly at the atmospheric pressure measured by the pressure sensor's low pressure port. In rigid container designs such as IV bottles (or in IV bags with pressure cuffs around them for increasing the fluid flow rate), this is not the case. A second embodiment of the present invention solves this problem by providing, in contrast to the gauge pressure sensing of the above designs, a differential pressure sensing capability. As shown in FIG. 4, since this embodiment of the invention may be used with rigid containers, the IV spike 66 used must have (in addition to the drip and vent assemblies) a spike high pressure tube 68 connecting a spike low pressure inlet port 70 to a spike low pressure outlet port 72 and a spike high pressure tube 74 connecting a spike high pressure inlet port 76 to a spike high pressure outlet port 78.

By connecting the low pressure port of the sensor 34 to the evacuated portion of the IV bottle 80, the pressure in the evacuated portion of the IV bottle 80 can be measured directly and used to determine the fluid level as follows. Referring to FIG. 4, assume that the height of the fluid surface from the bottom of the IV bottle 80 is h. Then, the pressure $P_E$ in the evacuated portion of the IV bottle 80 is given by $$P_E = P_A - \rho g h \qquad (1)$$

where $P_A$ is atmospheric pressure, $\rho$ is the density of the fluid, and g is the force due to gravity. Further, if the vertical distance between the high and low pressure inlet ports (preferably about 1") is $h_p$, then the pressure $P_L$ at the low pressure inlet port is similarly given by $$P_L = P_A - \rho g (h - h_p) \qquad (2)$$

and the pressure at the high pressure inlet port is $P_A$, since it is effectively equalized by the vent assembly. The pressure differential between the low and high pressure inlet ports is then $$\begin{aligned} \Delta P &= P_L - P_H \qquad (3) \\ &= P_A - \rho g (h - h_P) - P_A \\ &= \rho g (h_P - h) \end{aligned}$$

Thus, $$h = h_p - \Delta P / \rho g \qquad (4)$$

Since all quantities on the right hand side of the equation are known ($\rho$ may be approximated as 1 if necessary), the height h of the fluid in the IV bottle 80 can be determined. Of course, the use of a differential pressure sensing arrangement such as the one described above requires appropriate modifications of the alarm circuitry as will be apparent to those of ordinary skill in the art.

Figure 5:
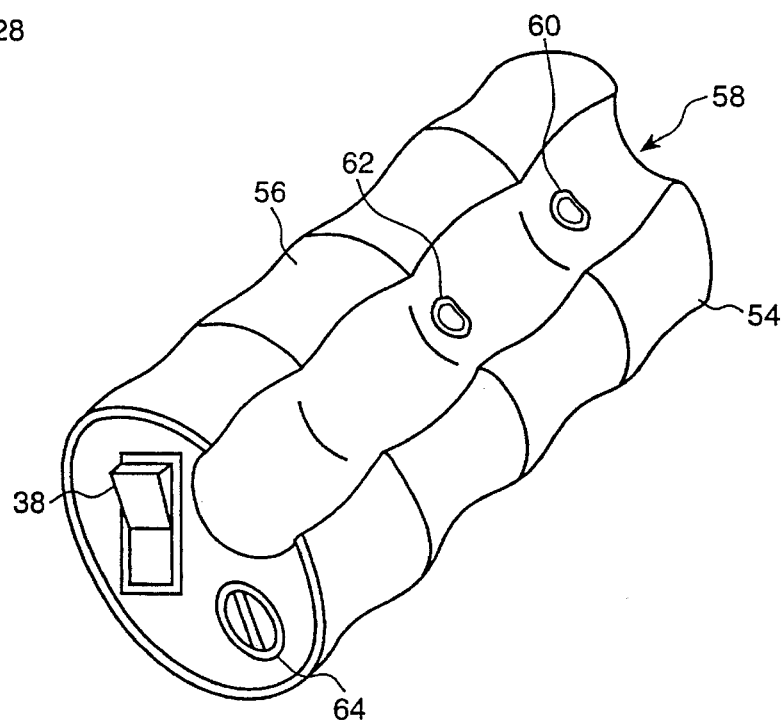
FIG. 5 is a perspective view of an IV spike holder suitable for use with the first and second embodiments of the invention.

The above designs will find use in a wide variety of applications; however, the separate units used for the IV spike 12 or 66, pressure sensor 34 and the alarm unit 34 make them unwieldy and somewhat cumbersome for frequent, everyday use. An alternative design has been developed to alleviate this problem. As can be seen in FIG. 5, rather than utilizing a specially adapted IV spike 12, this design uses a spike holder 54 engaging a conventional IV spike. The spike holder 54 is essentially cylindrical in shape and its curved surface 56 may be knurled to facilitate being grasped by medical personnel. The spike holder 54 has a recess 58 longitudinally extending along one side which can receive the IV spike body 26. The surface of recess 58 has a holder high pressure port 60 which mates with the vent outlet port 18 of the IV spike 12 and a holder low pressure port 62 which, in the first embodiment of the invention, exits to atmosphere, and in the second embodiment of the invention is connected to the spike low pressure assembly. As in the first embodiment, the sensor ports should be covered by microfiltration membranes to prevent contamination of the infusion fluid.

Figure 6A:
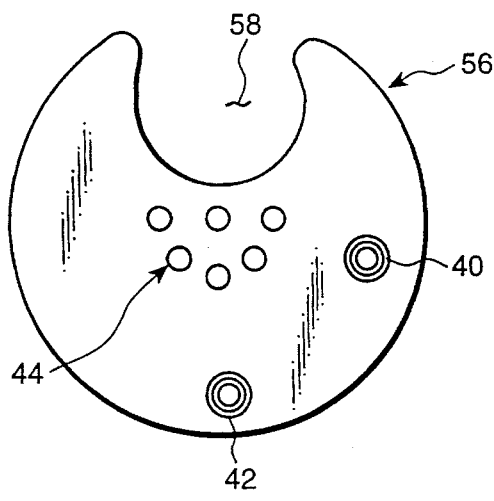
FIGS. 6A and 6B are end views of the spike holder of FIG. 5.
Figure 6B:
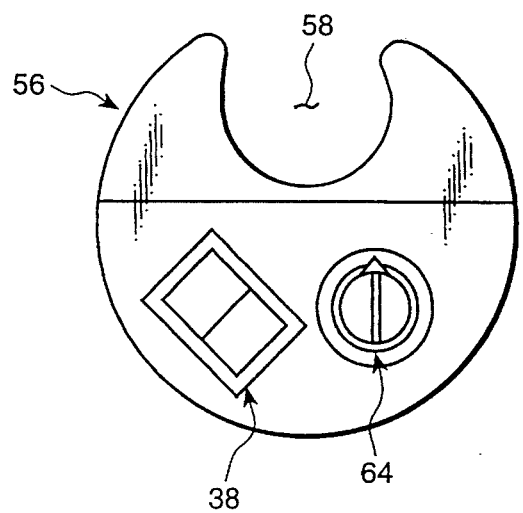

As shown more clearly in FIG. 6A, one end of the spike holder 54 has an ON/OFF switch and, in the second embodiment of the invention, a range adjustment control 64 as described above. As can be seen in FIG. 6B, the other end of the spike holder 54 may have a speaker 44, a POWER ON LED 40 and a LOW LEVEL LED 42.

Figure 7:
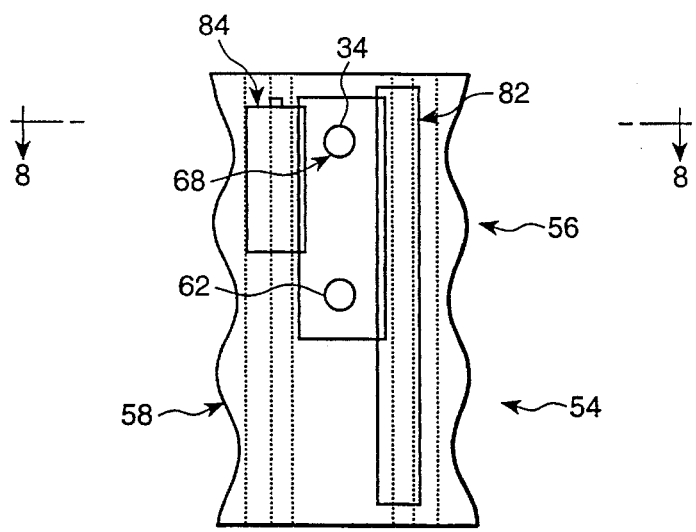
FIG. 7 is a partial cutaway view showing the construction of the spike holder of FIG. 5.
Figure 8:
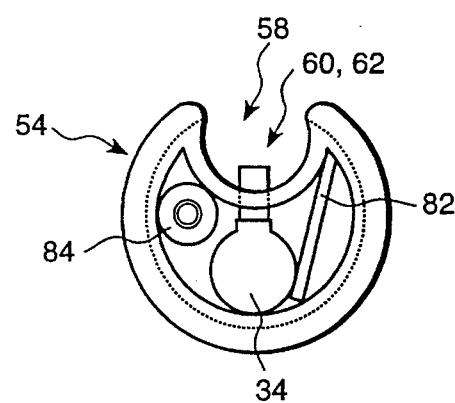
FIG. 8 is a cross-sectional view of the spike holder along line 8—8 in FIG. 7.

The internal construction of the spike holder 54 is shown more clearly in partial cut-away in FIG. 7 and in cross-section in FIG. 8, in which pressure sensor 34, circuit board 82, and battery 84 can be seen.

It is important to note that a fluid level monitor according to the present invention essentially comprises two portions: a first portion (i.e., the IV spike) that must be sterilized to avoid contamination of the fluid) and a second portion (i.e., the pressure sensor and associated circuitry) that need not be sterilized since it does not contact the fluid directly. This arrangement is advantageous since the sterile portion is relatively inexpensive (e.g., IV spikes currently cost less than one dollar each) and can be disposed after a single use, while the more expensive non-sterile portion can be used numerous times.

In lieu of the pressure sensor 34, the invention may use a resistive or capacitive sensor. In its simplest form, this type of sensor may be a pair of electrodes immersed in the infusion fluid. When the liquid level falls below the electrical sensor, its state changes, and the alarm circuitry is activated.

An example of an electrical sensor 88 according to this alternative embodiment of the present invention is illustrated in dashed lines in FIG. 4. Terminals 90 connect electrical sensor 88 to external circuitry. The circuit of FIG. 3 is particularly useful in this application, since the signals the ULM 2429A integrated circuit applies to the electrodes is an alternating current, thereby preventing the buildup of electrolytes thereon.

Although a few preferred embodiments of the invention have been shown and described, it will be appreciated by those skilled in the art that changes may be made in these embodiments without departing from the principles and the spirit of the invention, the scope of which is defined in the appended claims.

What is claimed is:

1. A fluid level monitoring system for a liquid container, said system comprising:

a pressure sensor operatively connected to an outlet of a liquid container, said pressure sensor receiving pressure exerted by liquid in said container and producing a signal indicative of a pressure levels;

an alarm responsive to said signal for providing at least one of a visual and an audible indication of said pressure level; and a spike having a first tube connecting a first inlet port to a first outlet port, said pressure sensor being operatively connected to said first outlet port.

2. The system of claim 1, wherein said pressure sensor is a switch.

3. The system of claim 1, wherein said pressure sensor is a piezo-responsive element.

4. A fluid level monitoring system as in claim 1, wherein said pressure sensor provides an output signal representative of a continuous range of pressures; and said alarm comprises means for selecting a threshold pressure level above which said indication is not provided and below which said indication is provided.

5. The system of claim 1, wherein said container is a medical infusion container and said spike is an IV spike.

6. The system of claim 1, further comprising:

a spike holder having a recess extending along one side, said recess accommodating a portion of said spike;

wherein said pressure sensor and said alarm are disposed within said spike holder.

7. The system of claim 6, said spike holder further comprising:

a high pressure port and a low pressure port each disposed on said cylindrically curved surface, said high pressure port being operatively connected to said first outlet port.

8. The system of claim 7, wherein said pressure sensor is a piezo-responsive element.

9. The system of claim 1, wherein said pressure sensor has a high pressure port and a low pressure port, said high pressure port being operatively connected to said first outlet port.

10. The system of claim 9, wherein:

said first tube, first inlet port and first outlet port are a vent tube, vent inlet port and vent outlet port, respectively; and said low pressure port exits to atmosphere.

11. The system of claim 10, wherein said high pressure port includes a filter preventing contamination of infusion liquid.

12. The system of claim 9, wherein:

said first tube, first inlet port and first outlet port are a high pressure tube, high pressure inlet port and high pressure outlet port, respectively;

said spike further comprises a low pressure tube connecting a low pressure inlet port to a low pressure outlet port and a vent tube connecting a vent inlet port to a vent pressure outlet port; and said sensor low pressure port is operatively connected to said low pressure outlet port.

13. The system of claim 12, wherein each of said high and low pressure ports include a filter preventing contamination of liquid.

14. The system of claim 12, wherein said low pressure inlet port is disposed approximately one inch away from said high pressure inlet port in a direction opposite to that of said outlet ports.

15. A fluid level monitoring system comprising:

a sensor connectable to an outlet of a liquid container which, said sensor operating in a first operating state if a level of said liquid in said container is at or exceeds a minimal threshold and in a second operating state if said level of said liquid drops below said minimal threshold, said sensor detecting said level of said liquid based on a characteristic of said liquid in said container and produces a signal indicative of said operating state;

an alarm responsive to said signal which provides at least one of a visual and an audible indication of said characteristic if said sensor enters said second operating state;

a spike having a first tube connecting a first inlet port to a first outlet port, wherein said sensor is disposed on said spike and immersible in said liquid to sense said liquid characteristic; and a spike holder having a substantially cylindrically curved surface longitudinally extending along one side, said surface defining a recess for accommodating a portion of said spike, wherein said alarm is disposed within said spike holder.

16. The system of claim 15, said sensing means further comprising:

a pair of contacts disposed on said cylindrically curved surface for making electrical connection with said pair of electrodes.

17. The system of claim 15, wherein:

said characteristic is liquid level; and said sensor comprises an electrical sensor disposed on said spike and immersible in said liquid.

18. The system of claim 15 wherein said container is a medical infusion container and said spike is an IV spike.

* * * * *